US008722038B2

(12) United States Patent
Mondovi' et al.

(10) Patent No.: US 8,722,038 B2
(45) Date of Patent: May 13, 2014

(54) HISTAMINASE OF VEGETABLE ORIGIN FOR USE IN THE TREATMENT OF ALLERGIC AND SEPTIC SHOCK AND OF ALLERGIC ASTHMA

(76) Inventors: Bruno Mondovi', Rome (IT); Olivia Befani, Rome (IT); Rodolfo Federico, Rome (IT); Mircea Alexandru Mateescu, Montreal (CA); Emanuela Masini, Florence (IT); Pier Francesco Mannaioni, Sesto Fiorentino (IT); Alfredo Vannacci, Prato (IT)

( * ) Notice: Subject to any disclaimer, the term of this patent is extended or adjusted under 35 U.S.C. 154(b) by 1254 days.

(21) Appl. No.: 12/217,447

(22) Filed: Jul. 3, 2008

(65) Prior Publication Data

US 2008/0279840 A1    Nov. 13, 2008

Related U.S. Application Data

(63) Continuation of application No. 10/433,075, filed as application No. PCT/EP01/13770 on Nov. 27, 2001, now abandoned.

(30) Foreign Application Priority Data

Nov. 29, 2000 (IT) ............................. RM2000A0626

(51) Int. Cl.
 *A61K 38/43*    (2006.01)
(52) U.S. Cl.
 USPC .......................................... 424/94.1; 424/810
(58) Field of Classification Search
 None
 See application file for complete search history.

(56) References Cited

U.S. PATENT DOCUMENTS

| | | | | |
|---|---|---|---|---|
| 3,721,733 | A | 3/1973 | van Leeuwen | 424/94.2 |
| 5,081,016 | A | 1/1992 | Hayashi et al. | 435/25 |
| 5,284,749 | A * | 2/1994 | Cowley et al. | 435/7.1 |
| 5,730,983 | A | 3/1998 | Wegner et al. | 424/185.1 |
| 6,299,886 | B1 | 10/2001 | Piper | 424/400 |

FOREIGN PATENT DOCUMENTS

FR     2 101 095    3/1972
FR     2 215 944    8/1974

OTHER PUBLICATIONS

US 5,725,540, Feb. 16, 1988, Underberg et al. (withdrawn).
Guvenilir, et al., "*The Isolation and Purification of Diamine Oxidase of Pea Seedling and Pig Liver*", Applied Biochemistry and Biotechnology; vol. 56, No. 3; pp. 235-241; Mar. 1996.
Yanagisawa, et al., "*Purification and Properties of Diamine Oxidase From Pea Epicytyls*", Phytochemistry; vol. 20, No. 9, pp. 2105-2108, Sep. 1981.
Suresh, et al., "*Diamine oxidase of Lathyrus sativus Seedlings, Purification and Properties*", Journal of Biosciences; Indian Academy of Sciences; vol. 1, No. 2, pp. 109-124; Jun. 1979.
Seipaio, et al., "*Diamine Oxidase and Transglutaminase Activities in White Lupine Seedlings with Respect to Cross-Linking of Proteins*", Journal of Agric. Food Chem.; vol. 43, pp. 1151-1156; 1995.
Coudhary, et al., "*A thermostable diamine oxidase from Vigna radiata Seedlings*", Phytochemistry; vol. 52, No. 1, pp. 1-5, Sep. 1999.
Kumar, V., et al., "Crystal structure of a eukaryotic (pea seedling) cooper-containing amine oxidase at 2.2 A resolution," Research Article, Structure, Aug. 15, 1996, 4:943-955.
Sobel, B.E., et al., "Augmented and Sustained Plasma Concentrations After Intramuscular Injections of Molecular Variants and Deglycosylated Forms of Tissue-Type Plasminogen Activators," Circulation, vol. 81, No. 4, Apr. 1990, pp. 1362-1373.
Sacco, A.G., et al., "Carbohydrafte influences the immunogenic and antigenic characteristics of the ZP3 macromolecule (Mr 55 000) of the pig zona pellucida," J. Reprod. Fer. (1986) 76, pp. 575-586.
Romain, F., et al., "Deglycosylation of the 45/47-Kilodalton Antigen Complex of *Mycobacterium tuberculosis* Decreases Its Capacity to Elicit In Vivo or In Vitro Cellular Immune Responses," Infection and Immunity, vol. 67, No. 11, Nov. 1999, pp. 5567-5572.
Obregon-Henaro, A., et al., "The role of N-linked carbohydrates in the antigenicity of *Taenia solium* metacestode glycoproteins of 12, 16 and 18 kD," Molecular & Biochemical Parasitology 114 (2001) pp. 209-215.

* cited by examiner

*Primary Examiner* — Debbie K Ware
(74) *Attorney, Agent, or Firm* — Klauber & Jackson LLC

(57) ABSTRACT

The present document describes a method of treating a histamine-mediated condition by administering an effective amount of a histaminase of vegetable origin to a subject in need. The histamine-mediated condition may be an allergic shock, septic shock, allergic asthma, anaphylaxis, rhinitis, allergic conjunctivitis, urticaria, atopic dermatitis, and pruritus.

8 Claims, No Drawings

HISTAMINASE OF VEGETABLE ORIGIN FOR USE IN THE TREATMENT OF ALLERGIC AND SEPTIC SHOCK AND OF ALLERGIC ASTHMA

CROSS-REFERENCED APPLICATIONS

This application is a Continuation Application of U.S. patent application, Ser. No. 10/433,075, filed on May 20, 2003, now abandoned, which is a national phase of PCT/EP2001/013770, filed Nov. 27, 2011, which is incorporated herein by reference.

BACKGROUND

1. Field of the Disclosure

The present disclosure relates to a histaminase of vegetable origin to be used in the treatment of allergic and septic shock and of allergic asthma. The disclosure also regards the preparation of the histaminase for pharmaceutical use and the corresponding pharmaceutical compositions.

2. Discussion of the Background Art

Histaminase is an enzyme of the family of the amine oxidases. A method for its preparation is described in the U.S. Pat. No. 4,725,540, where histaminase is produced by microorganisms and used for removing or degrading the histamine present in animal feed and in those foods that may be responsible for allergies, such as milk and its derivatives, so as to stem allergic phenomena affecting humans. Afterwards, histaminase is removed or in some way deactivated by the above-mentioned types of food.

Allergy is a complex phenomenon that may even affect internal organs, such as the heart and the lungs, causing bronchospasm, dyspnoea, asthma and shock. In particular, asthma is a chronic inflammatory state of the airways, in which numerous cells of the immune system co-operate, and which generates, in predisposed subjects, a constriction of the air flow at the bronchial level, with episodes of dyspnoea, breathlessness, thoracic oppression and coughing. The growing number of people in the world that suffer from asthma is a cause of great concern; today they amount to approximately 200 million (data issued by the World Health Organization). In 1997, 180,000 patients died from asthma (Humbert M., Le Scienze, 381, May 2000).

Histamine is the principal chemical mediator of the first phase of allergic reactions, and it is also known that many of the drugs currently available and used for the treatment of these clinical situations interact to some extent with this substance both by interfering with its release and by blocking its action at a receptor level.

Asthma and allergic shock have so far been treated using drugs, amongst which corticosteroids, anti-$H_1$ anti-histamines, $\beta_2$ stimulants and, in more serious forms, adrenaline. However, the above drugs present negative side effects.

In the treatment of allergic asthma and of allergic diseases in general, a basic therapy and an acute-attack therapy are known. In the immediate treatment of an attack of asthma, certainly by far the most effective drugs are the $\beta_2$ agonists, in particular salbutamol. However, these drugs must be considered only symptomatic, in so far as they induce relaxation of smooth bronchial muscle without affecting at all the pathogenic mechanism of the allergic reaction. In addition, the effect of inhibition of the release of mediators of mast cells, which has been demonstrated for salbutamol in vitro and in vivo, is not, however, detectable in clinical use, given the acute conditions under which the drug is administered, as well as the brief duration of its action. Salbutamol and $\beta_2$ agonists in general, notwithstanding the encouraging results obtained in in-vitro models and in experimental animals (for example, guinea pigs), have revealed, when administered to humans in the course of illness, the onset of important side effects, such as tachycardia, arrhythmias, tremors, cephalea, nausea, and vomiting (Ahrens R. C., Smith G. D., Albuterol: An adrenergic agent for use in the treatment of asthma; pharmacology, pharmacokinetics and clinical use. Pharmacotherapy, May-June 1984; 4 (3): 105-21).

Another drug indicated both in attacks of asthma and in anaphylactic shock on account of its marked $\beta_2$-agonist action is adrenaline, a drug which is certainly effective and frequently a life-saver in emergency situations, but which also presents dangerous side effects (hyperglycaemia, dyspnoea, tachycardia, arrhythmias, cephalea, vomiting, and dizziness, up to the point of triggering attacks of angina in cardiac patients), which relegate its use only to life-threatening situations (Hoffman B. B., Lefkowitz R. J., Catecholamines, sympathomimetic drugs and adrenergic receptor antagonists. In: Goodman and Gilman, The pharmacological basis of therapeutics, 9th edition. 199-248, 1996).

Ipratropium bromide, an $M_3$ muscarine-receptor-antagonist drug for acetylcholine, has demonstrated a certain degree of efficacy as bronchodilatator and is considered a drug of second choice after $\beta_2$ stimulants, compared to which it is less effective, but also better tolerated (Lovine R. R. Ed., Subtype of muscarine receptors. VI Life Sci. 1995, 56: 801, 1002).

The use of methyl xanthines via parenteral route, which are useful above all in the state of asthmatic illness, is extremely dangerous owing to the considerable systemic effects (risk of arrhythmias, panic attacks, convulsions), which limit their use to the more serious situations and involve the need for careful monitoring of the patient (Nasser S. S., Rees P. J., Theophylline. Current thoughts on the risks and benefits of its use in asthma. Drug Saf. January 1993; 8 (1): 12-8).

As far as basic treatment is concerned, the corticosteroids are the most effective drugs in the prevention of allergic reactions and present an action that is not only symptomatic, but also able to abolish some of the pathogenic mechanisms that underlie immuno-allergic phenomena. Their efficacy is beyond doubt both in attenuating the phenomenon in the acute phase and in the prevention of long-term relapse; however, in this case, the numerous side effects of these drugs inevitably emerge (hyperglycaemia, osteoporosis, suppression of the hypothalamus-pituitary-adrenal axis, dysphoria/depression, increase in weight, hydro-saline retention, gastro-duodenal ulcer, cataract, hypertension, immuno-suppression, suspension syndrome) (Lipworth B. J., Clinical pharmacology of corticosteroids in bronchial asthma. Pharmacol. Ther. 1993; 58 (2): 173-209).

$H_1$ anti-histamines have for some time now represented one of the corner stones in the treatment of allergic phenomena. Their action is based upon the occupation of the $H_1$ receptor (responsible for the effects of bronchoconstriction and cutaneous and mucous vasodilation), so that the histamine released by the immuno-phlogosis cells cannot express its action. Their acute effect is not particularly important, and they are in fact effective especially in the long-term prevention of attacks of asthma and of allergic cutaneous reactions. Their main side effects are at the level of the central nervous system (drowsiness) and of the gastro-intestinal apparatus (nausea, vomiting, epigastralgia, alterations of the alvus) (Holgate S. T., Antihistamines in the treatment of asthma. Clin. Rev. Allergy Spring 1994; 12 (1): 65-78).

The chromones (disodium chromoglycate, Nedocromil sodium) are used in the prevention of asthma attacks and above all of allergic rhinitis on account of their properties for stabilizing the mast-cell membrane; they do not present particular side effects (rare cases of sensitization, cephalea and nausea are reported) but have a modest efficacy, even in the mild forms of asthma (Brogden R. N., Sorkin E. M., Nedocromil sodium. An updated review of its pharmacological properties and therapeutic efficacy in asthma. Drugs, May 1993; 45 (5): 693-715).

Leukotriene-receptor antagonists (Zafirlukast, Montelukast) have recently proved useful for reducing the use of corticosteroids in the prevention of asthma attacks in mild-to-moderate forms; however, their action starts to appear only after 2 weeks of treatment (Diamant Z., Sampson A. P., Anti-leukotriene therapy for asthma. In: Anti-inflammatory drugs in asthma. Sampson & Church Eds., Birkäuser, Basel, 1999).

From the foregoing it emerges how, notwithstanding the constant endeavour aimed at countering allergic phenomena, given their enormous negative impact on the world population, so far no effective means have come available. The need was thus felt for the development of an effective drug and one exempt from side effects for the treatment of allergies in general, and of asthma and allergic and septic shock in particular.

SUMMARY OF THE DISCLOSURE

It is an object of the present disclosure to make available a histaminase-based drug of vegetable origin to be used in the medical field, in particular for the treatment of allergies in general and of anaphylactic reactions in particular. Another object of the disclosure is to make available a drug for the treatment of histamine-mediated affections.

A further object of the disclosure is the use of a particular histaminase (Enzyme Commission EC 1.4.3.6) of vegetable origin that presents, amongst its innumerable advantages, a considerable ease of production, a high stability and a high level of activity.

Another object is the method of production of the histaminase of vegetable origin for pharmaceutical purposes.

Further objects are the pharmaceutical compositions comprising, as active principle, the histaminase of vegetable origin, and the corresponding dosages and administration protocols.

Still another object is represented by the injectable and spray pharmaceutical formulations.

Further objects will emerge clearly from the detailed description of the disclosure.

DETAILED DESCRIPTION OF THE PREFERRED EMBODIMENT

Characteristics and advantages offered by the histaminase of vegetable origin to be used as active principle in the treatment of allergies will be described in detail in what follows.

In the present description the term "histaminase" is meant to embrace the entire class of copper amine oxidases of plants (known to a person skilled in the branch) in so far as they all have the same mechanism of action for the purposes of the present disclosure.

The experimental tests for verifying the pharmaceutical activity of the histaminase were initially conducted by the present authors on two classic models for the study of immuno-allergic phenomena: (i) cardiac anaphylaxis obtained in vitro on isolated hearts taken from previously sensitized guinea pigs and subjected to Langendorff perfusion and re-exposed to the antigen; and (ii) allergic asthma evoked by the antigen in sensitized guinea pigs in vivo. These tests revealed that protection was achieved both from an evaluation of the mechanical parameters and from an evaluation of the biochemical indices modified during cardiac anaphylaxis and allergic asthma.

The above results, albeit encouraging, are, however, not resolutive. In fact, even though the guinea pig is a mammal with an aminergic system similar to that of man (in fact, in guinea pigs histamine has a preferential atrio-ventricular right-left distribution similar to its distribution in the human heart, and hence provides an animal model that is universally utilized for the study of the physio-pathological histamine-mediated processes) (Cairns H., Models for the development of anti-asthmatic drugs. In: The mast cell: its role in health and disease. Pepys & Edwards Eds., Pitman, London, 1979), the extrapolation to man of the experimental results obtained in the guinea pig is neither justified nor, much less, obvious. Although it is absolutely indispensable to obtain positive results in laboratory animals before administration of potentially active molecules to a healthy volunteer for pathological situations, it is not at all certain that in man there will be the same results, in so far as there exist pharmacokinetic diversities (of absorption, distribution and accumulation in blood cells and in the organs) that may modify significantly the bioavailability of the drug, its pharmacological activity and hence its therapeutic effect. Furthermore, the possible untoward side effects fail absolutely to be inferable. The tests on guinea pigs are therefore not a direct and unequivocal proof of the efficacy of the enzyme in humans in so far as the human immuno-allergic disease is far more complex than any experimental model (e.g., isolated organ in vitro) since it is characterized by a complex pathogenic model that involves more than one mediator responsible for the clinical symptoms and signs.

In addition, there exists a technical prejudice according to which histaminase does not present any protective effect against allergies (Lessico Universale Italiano Treccani—Istituto Enciclopedico Italiano Vol. VI, 1970 at the entry: diamminossidasi)

In tests carried out in vivo, the histaminase was utilized via systemic (intraperitoneal) route, whereas subsequently the activity was verified also via inhalatory route.

The authors suggest that in man histaminase can be used in the treatment of allergic and septic shock, in allergic asthma and in general in all histamine-mediated affections, such as allergic rhinitis and conjunctivitis, urticaria and atopic dermatitis. In addition, its usefulness is to be expected in the symptomatic control of pruritus of various origin.

For this use histaminase of vegetable origin has proven suited on account of its ease of production and owing to its stability and high activity, and histaminase isolated from leguminous plants has proven particularly suited.

It has been verified that histaminase acts directly on the fundamental effector of the allergic response, degrading the histamine released at the moment of the event that triggers the reaction, before its effects start to appear. Consequently, the allergic phenomenon is blocked instantaneously.

The source of histaminase of vegetable origin is constituted preferably by etiolated seedlings of leguminous plants, such as *Pisum sativum L., Lens culinaris, Cicer arietinum*, and *Lathyrus sativus*, as well as corresponding mixtures.

To obtain the enzyme, the vegetable material (in general, etiolated seedlings of approximately 10 days old) is homogenized, the homogenization being a procedure known to a person skilled in the art, in acidic condition, namely, at pH<7, preferably at pH<5.5 in phosphate buffer at low ionic strength (<100 mM). Particularly preferred is homogenization conducted with phosphate buffer, approximately 50 mM, pH 3.5-5. The homogenate thus treated is then subjected to extraction and purification according to conventional procedures known to a person skilled in the art.

The stage of homogenization referred to above is advantageous in that it makes it possible to obtain, in an extremely simplified way, as starting product for the subsequent extraction, only the proteins bonded ionically to the cell walls and in general to the corpusculated fractions, and not the total soluble proteins. Consequently, it is possible to obtain the enzyme with a high degree of purity with just two chromatographic passes, which are simple and inexpensive.

The protein purified using this method is characterized by a high specific activity (in the region of 60 UE/mg, where UE (enzymatic unit) is the quantity of protein that catalyses the conversion of one μmole of substrate per minute), appears homogeneous in electrophoresis, and presents spectroscopic characteristics typical of histaminase. The chemico-physical and enzymatic characteristics of the enzyme purified by us match those of the pure enzyme described in the literature. (Kumar et al., Crystal structure of Eukaryotic (pea seedling) copper containing amine oxidase. Structure, 1996, vol. 4, par. 8, pp. 943-955).

For the purposes of the disclosure, it is also possible to use histaminase immobilized on a biocompatible insoluble matrix. For example, the histaminase was bound on CNBr-activated Sepharose 4B® and on Activated CH-Sepharose 4B®, following the procedures recommended by the supplier of the resins (Amersham, Pharmacia-Biotech). The immobilized enzyme, in both formulations, proved more resistant to hydrolysis catalysed by proteolithic enzymes as compared to the free enzyme.

Once purified, the enzyme may be lyophilized using known techniques; the enzyme thus prepared is stable for various months. The pharmaceutical preparations may be prepared with this lyophilized enzyme.

The lyophil is dissolved at the moment of use in the solvent (e.g., apyrogenic physiological solution buffered at pH 7.4 or other iso-osmotic solutions) and injected, for instance via parenteral route, in emergency treatment of anaphylactic and septic shock and in the state of asthmatic disease. The enzyme in sterile solution maintains its own activity practically unaltered for at least 15 days at room temperature.

The spray form is particularly indicated in the treatment of acute attacks of asthma and in its daily prophylaxis.

The pharmaceutical compositions containing the histaminase may be obtained by mixing together effective quantities of the active principle with diluents and/or excipients known to a person skilled in the art to obtain injectable formulations, for example administrable by parenteral route, or spray formulations.

The disclosure also relates to the treatment of histamine-mediated affections in general and of allergies in particular, consisting in the administration of pharmacologically acceptable doses of histaminase. The doses and the modalities of administration vary according to the type and gravity of the affection. Therapeutic dosages may be recommended ranging between 0.01 mg and 1 mg per administration.

The advantages of the administration of vegetable histaminase to humans and of the corresponding pharmacological preparations are the following:
   direct (unmediated) action on the allergic process, in so far as histaminase acts in the organism directly on the histamine, eliminating it by oxidation, unlike the drugs currently available on the market, which act only by reducing the amount of the allergic response once this has already been set up;
   absence of toxicity and substantial absence of side effects currently demonstrated;
   presumable maintenance of the therapeutic efficacy also in long-term treatments (no tolerance demonstrated).

The following examples are given to illustrate the disclosure and are not to be considered in any way limiting of the scope thereof.

EXAMPLE 1

The vegetable material (500 g of etiolated seedlings of *Pisum sativum L.* of approximately 10 days old) is homogenized with 2 liters of a phosphate buffer 50 mM, pH 4.2. The homogenate is appropriately filtered, and the residue, which consists prevalently of cell walls, vascular fibres and sub-cellular organelles, is washed with a liter of the same buffer. The material thus obtained is extracted with 0.5 liters of a 20% saturated solution of ammonium sulphate in a phosphate buffer 50 mM, pH 4.2. Ammonium sulphate is added to the solution thus obtained up to a saturation of the 70%, the solution being then left for two hours at 4° C. and then centrifuged at 7000 r.p.m. for 30 minutes. The precipitate is diluted with 0.2 liters of phosphate buffer 50 mM, pH 7.2, and dialysed against the same buffer.

Upon completion of dialysis, the solution undergoes chromatography using a column of diethylaminoethyl-cellulose (DEAE-Cellulose), volume of the gel 0.3 liters, previously equilibrated with phosphate buffer 15 mM, pH 7.2. In these conditions, the histaminase is not bound to the matrix and is contained in the effluent.

The effluent of the DEAE is charged on a column of hydroxyl appetite, volume of the gel 0.03 liters, previously equilibrated with phosphate buffer 15 mM, pH 7.2. The column is washed with phosphate buffer 30 mM, pH 7.2, and eluted with a linear gradient of concentration of phosphate buffer, pH 7.2, between 50 and 180 mM. The fractions with highest specific activity, understood as enzymatic activity per amount of total protein, are re-united and represent the purified preparation of the enzyme histaminase.

The enzyme is then lyophilized starting from a solution of the histaminase in phosphate buffer 10 mM pH 7.4 containing NaCl 0.15 M.

EXAMPLE 2

The lyophilized enzyme is readily soluble in apyrogenic bi-distilled water up to a volume equal to the starting volume for lyophilization. For use, a single dose containing from 10 mcg to 1 mg of enzyme is administered.

EXAMPLE 3

Tests of administration to healthy volunteers have not revealed any untoward side effects.

What is claimed is:
1. A method of treating a histamine-mediated condition comprising the step of administering an effective amount of a hydroxylapatite purified histaminase of vegetable origin to a subject in need, wherein said histamine-mediated condition is selected from the group consisting of allergic shock, septic shock, allergic asthma, anaphylaxis, rhinitis, allergic conjunctivitis, urticaria, atopic dermatitis, and pruritus,
   wherein said histaminase of vegetable origin has a low content in carbohydrate for improving stability and circulation time, and lower antigenecity of said histaminase of vegetable origin.
2. The method according to claim 1, wherein the histaminase is administered as an injectable formulation.

3. The method according to claim 1, wherein the histaminase is administered as a spray formulation.

4. The method according to claim 1, wherein the histaminase is immobilized on a biocompatible insoluble matrix.

5. The method according to claim 1, wherein the histaminase is administered in concentrations ranging between about 0.01-1 mg per administration.

6. The method according to claim 1, wherein said histaminase is derived from vegetable material that is selected from the group consisting of *Pisum sativum L., Lens culinaris, Cicer arietinum, Lathyrus sativus*, and mixtures thereof.

7. The method according to claim 1, wherein the histaminase is in lyophilized form and, at the moment of administration, is dissolved in a solvent comprising apyrogenic physiological solution that is buffered at pH 7.4.

8. The method according to claim 1, wherein the histaminase has high specific activity in the region of 60 UE/mg (enzymatic units per milligram).

* * * * *